(12) United States Patent
Mollat et al.

(10) Patent No.: US 7,776,625 B2
(45) Date of Patent: Aug. 17, 2010

(54) METHOD FOR LOCATING A SUB-SURFACE FEATURE USING A SCATTEROMETER

(75) Inventors: Martin B. Mollat, McKinney, TX (US);
Christopher C. Baum, Richardson, TX (US); Jonathan W. VanBuskirk, Royce City, TX (US)

(73) Assignee: Texas Instruments Incorporated, Dallas, TX (US)

( * ) Notice: Subject to any disclaimer, the term of this patent is extended or adjusted under 35 U.S.C. 154(b) by 185 days.

(21) Appl. No.: 11/423,209

(22) Filed: Jun. 9, 2006

(65) Prior Publication Data

US 2007/0287204 A1    Dec. 13, 2007

(51) Int. Cl.
*H01L 21/66* (2006.01)
(52) U.S. Cl. .................. 438/14; 438/401; 257/E21.521
(58) Field of Classification Search .................. 438/14, 438/401; 257/E21.521
See application file for complete search history.

(56) References Cited

U.S. PATENT DOCUMENTS

| | | | | |
|---|---|---|---|---|
| 3,971,059 A | * | 7/1976 | Dunkley et al. | 257/549 |
| 5,172,188 A | * | 12/1992 | Nagoya | 356/614 |
| 2003/0190793 A1 | * | 10/2003 | Brill et al. | 438/401 |

OTHER PUBLICATIONS

Logofatu et al. "Scatterometry, an optical methology technique for lithography", IEEE, 2004, pp. 517-520.*

* cited by examiner

*Primary Examiner*—Asok K Sarkar
*Assistant Examiner*—Julia Slutsker
(74) *Attorney, Agent, or Firm*—Wade J. Brady, III; Frederick J. Telecky, Jr.

(57) ABSTRACT

The present invention provides a method for manufacturing a semiconductor device. The method for manufacturing the semiconductor device, without limitation, may include providing a substrate having a sub-surface feature and a surface feature, and determining a location of the sub-surface feature relative to the surface feature using a scatterometer.

17 Claims, 3 Drawing Sheets

METHOD FOR LOCATING A SUB-SURFACE FEATURE USING A SCATTEROMETER

TECHNICAL FIELD OF THE INVENTION

The present invention is directed, in general, to a method for locating a sub-surface feature and, more specifically, to a method for locating a sub-surface feature using a scatterometer.

BACKGROUND OF THE INVENTION

Analog circuits, whether alone or as part of a mixed-signal integrated circuits (ICs), are particularly susceptible to substrate noise. In mixed signal ICS, the analog circuits are designed on the same semiconductor chip as digital circuits. Consequently, since the analog circuits share the same substrate with high-speed digital circuits, electrical noise created by the high-speed operation is coupled between the circuits and may affect the performance of the analog circuits. As the frequency of the operational digital circuit increases, and transistor dimensions are reduced, the effect of noise coupling is becoming more and more serious for the analog circuits, particularly. Similar problems may also exist for ICs including only analog circuits, as opposed to mixed signal ICs.

The industry has, in an attempt to reduce substrate noise, turned to the use of heavily doped buried layers (e.g., heavily doped buried N-type and P-type layers). Other industries, especially those including specialized High Voltage components (e.g., FET's, SCR's and Diodes as well as BJT components) also use heavily doped buried layers to enable a sub-surface region of low resistivity and achieve required performances. For technologies employing such heavily doped buried layers, epitaxial silicon is grown over such buried layers after their formation. However, epitaxial lattice shift, particularly acute when using off-axis silicon substrates, often results in misalignment with the heavily doped buried layers. The result of the unknown epitaxial lattice shift, at least in one instance, is a misalignment between the heavily doped buried layers edges and the well edges formed thereover. This is particularly problematic for high voltage wells, which may lead to significant leakage paths or changes in the high voltage component capability. No known method for measuring epitaxial lattice shift in a non-destructive manner on product wafers currently exists.

An urgent need has, therefore, arisen for a method for accurately measuring epitaxial silicon shift, such that the aforementioned misalignments between sub-surface features (e.g., heavily doped buried layers in one instance) and surface features (e.g., well structures in one instance) may be reduced.

SUMMARY OF THE INVENTION

To address the above-discussed deficiencies of the prior art, the present invention provides a method for manufacturing a semiconductor device. The method for manufacturing the semiconductor device, without limitation, may include providing a substrate having a sub-surface feature and a surface feature, and determining a location of the sub-surface feature relative to the surface feature using a scatterometer.

In an alternative embodiment, the method for manufacturing the semiconductor device includes providing a wafer substrate having a doped buried layer located thereover and forming an epitaxial layer over the doped buried layer, the epitaxial layer having a surface feature. The method further includes determining a location of the doped buried layer relative to the surface feature using a scatterometer, and forming an additional feature over, on or in the epitaxial layer using the determined location.

The present invention further provides a semiconductor device. The semiconductor device, among other features, includes: (1) a doped buried layer located over a wafer substrate, (2) an epitaxial layer located over the doped buried layer and having a surface feature, and (3) an additional feature located over, on or in the epitaxial layer, the additional feature aligned with respect to the doped buried layer by determining a location of the doped buried layer relative to the surface feature using a scatterometer.

BRIEF DESCRIPTION OF THE DRAWINGS

For a more complete understanding of the present invention, reference is now made to the following descriptions taken in conjunction with the accompanying drawings, in which.

DETAILED DESCRIPTION

The present invention is based, at least in part, on the acknowledgement that a location of a sub-surface feature may be determined using a scatterometer. For instance, the present invention has acknowledged that a scatterometer, which is typically only used to observe and locate surface features, may be used to determine the location of the sub-surface feature relative to a surface feature. For example, the scatterometer might, by measuring a diffraction pattern, be used to find a location of a doped buried layer (e.g., a sub-surface feature) relative to a subsequently formed surface feature (e.g., a relief feature associated with the doped buried layer and carried to the surface of the epitaxial layer during the formation of the epitaxial layer). In one instance, this allows any epitaxial lattice shift that occurs after formation of the doped buried layer to be identified, and the appropriate correction to be made in subsequent manufacturing processes. To date, no such non-destructive sub-surface location methodology, particularly one having the ease of use of the present invention, exists.

Figure 1:
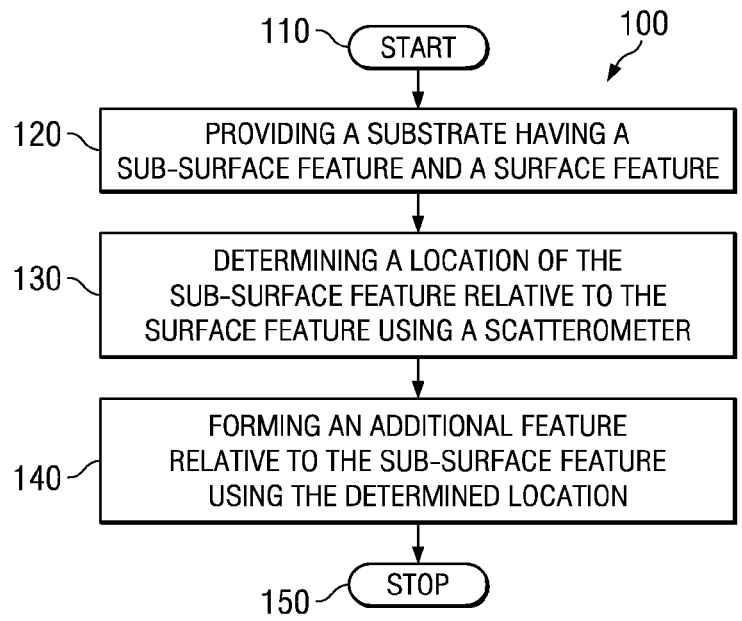
FIG. 1 illustrates a flow diagram of a method of manufacturing a semiconductor device in accordance with the principles of the present invention.

Turning to FIG. 1 illustrated is a flow diagram 100 of a method of manufacturing a semiconductor device in accordance with the principles of the present invention. The flow diagram 100 sets forth but one embodiment of a method of manufacturing a semiconductor device in accordance with the principles of the present invention. Accordingly, other embodiments exist using different steps than those illustrated in FIG. 1.

The flow diagram 100 of FIG. 1 begins with a start step 110. In a step 120, a substrate having a sub-surface feature and a surface feature is provided. The substrate, as those skilled in the art appreciate, may comprise many different materials and configuration while remaining within the purview of the present invention. In one embodiment, the substrate comprises a single layer of material having a feature buried therein and having a surface feature thereon or thereover. In another embodiment, which will be discussed more thoroughly below with respect to FIGS. 2 thru 6, the substrate comprises a wafer substrate having an epitaxial layer located thereover. For instance, the sub-surface feature might be a doped buried layer located between the wafer substrate and the epitaxial layer, and the surface feature might be a relief feature in the upper surface of the epitaxial layer. In essence, the substrate may comprise any one or collection of layers located in a semiconductor, microelectronics, optoelectronics, nano technology, or other similar device, including a layer located at wafer level or a layer located above or below wafer level.

In a step 130, after providing the substrate, a location of the sub-surface feature relative to the surface feature may be determined using a scatterometer. In the embodiment wherein the sub-surface feature is a doped buried layer and the surface feature is the relief feature, the scatterometer may be used to determine the location of the doped buried layer relative to the relief feature. As the relief feature is related to the doped buried layer, the location of the doped buried layer relative to the relief feature is instructive in determining an amount of epitaxial lattice shift in the epitaxial layer. The determination of the epitaxial lattice shift is particularly advantageous when the wafer substrate is an off-axis (e.g., crystal orientation) silicon substrate, as is often the case in today's emerging technologies.

Thereafter, in a step 140, an additional feature may be formed relative to the sub-surface feature using the determined location (e.g., lateral location in one embodiment). Thus, in the instant embodiment wherein the sub-surface feature is the doped buried layer, the determined location may be used to position one or more isolation well features, among other known features, relative to the doped buried layer. In many instances, such precise alignment is desired, if not required, to reduce leakage paths in the semiconductor device being formed. At this stage of manufacture, the process might repeat steps 120 thru 140 on a different substrate, or alternatively stop at step 150.

Figure 2:
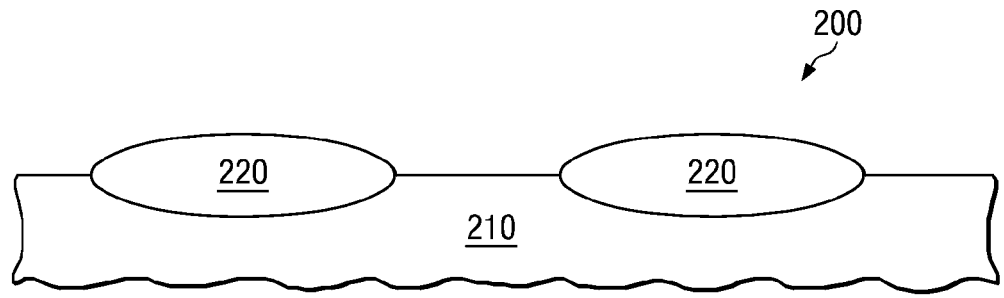
FIGS. 2 thru 6 illustrate sectional views showing how one might, in an embodiment, manufacture a semiconductor device in accordance with the principles of the present invention.

Turning now to FIGS. 2 thru 6, with brief references to FIG. 1, illustrated are sectional views illustrating how one might, in an embodiment, manufacture a semiconductor device 200 in accordance with the principles of the present invention. FIG. 2 illustrates a sectional view of a wafer substrate 210 having one or more doped buried layers 220 located therein, thereon or thereover. In the given embodiment shown, the doped buried layers 220 are formed at least partially in and at least partially over the wafer substrate 210. Likewise, the doped buried layers 220 of FIG. 2 are formed in repeating grid spacing, such that a scatterometer might be used to determine their location.

Those skilled in the art of doped buried layers, particularly heavily doped n-type and p-type buried layers, understand the processes that might be used for their formation. For instance, the doped buried layers 220 may be formed by implanting an n-type or p-type dopant at precise locations within the wafer substrate 210. For example, conventional implantation processes might be used to form the one or more doped buried layers 220.

Figure 3:
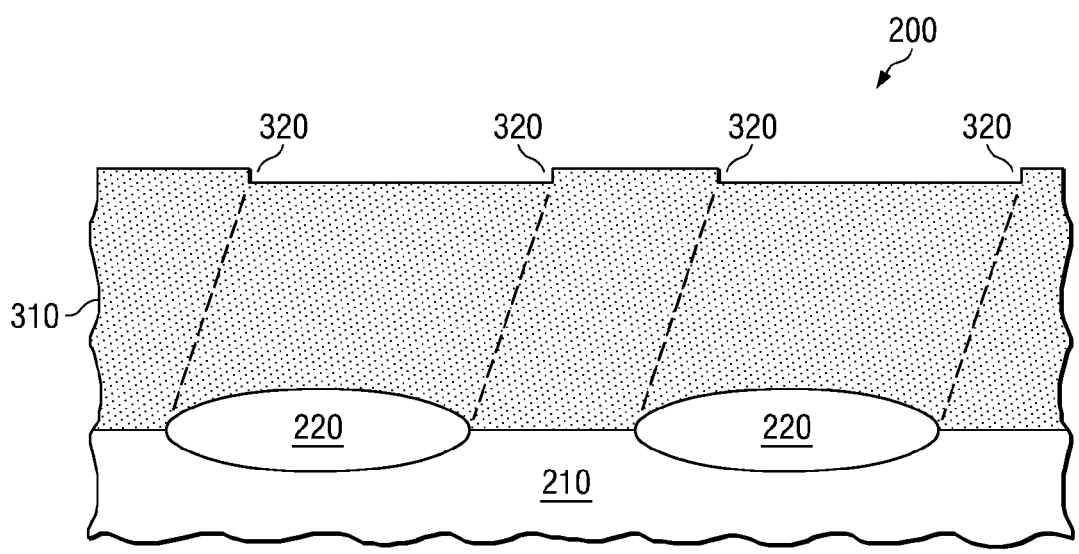

Turning now to FIG. 3, illustrated is the semiconductor device 200 of FIG. 2 after formation of an epitaxial layer 310 over the wafer substrate 210. Accordingly, in the embodiment shown in FIG. 3, the doped buried layers 220 are located between the wafer substrate 210 and the epitaxial layer 310, and thus are sub-surface features. Depending on the specific application, the epitaxial layer 310 may have a thickness ranging from about 3.0 microns to about 8.0 microns, among others.

Located in an upper surface of the epitaxial layer 310 in the embodiment of FIG. 3 are one or more surface features 320. In the particular embodiment shown, the one or more surface features are relief features. For example, the one or more relief features may be associated with the doped buried layers 220, and more specifically relief features that are directly related to the doped buried layers 220 but carried to the surface of the epitaxial layer 310 during the formation thereof. Accordingly, in the embodiment of FIG. 3, each of the lateral edges of the doped buried layers 220 have a related surface feature 320.

The surface features 320 of FIG. 3 illustrate but one embodiment of surface features. Another embodiment exists wherein the surface features are not the illustrated relief features, but are features related to another structure of the semiconductor device. Accordingly, the present invention should not be limited to the relief features illustrated in FIG. 3.

The epitaxial layer 310, as one would expect, may be manufactured using many different processes, whether conventional or not. For example, in one embodiment the epitaxial layer 310 may be deposited using standard techniques. Whether the process for forming the epitaxial layer 310 is conventional or not, at least in the embodiment shown, the surface features 320 will generally arise to the surface thereof.

Figure 4:
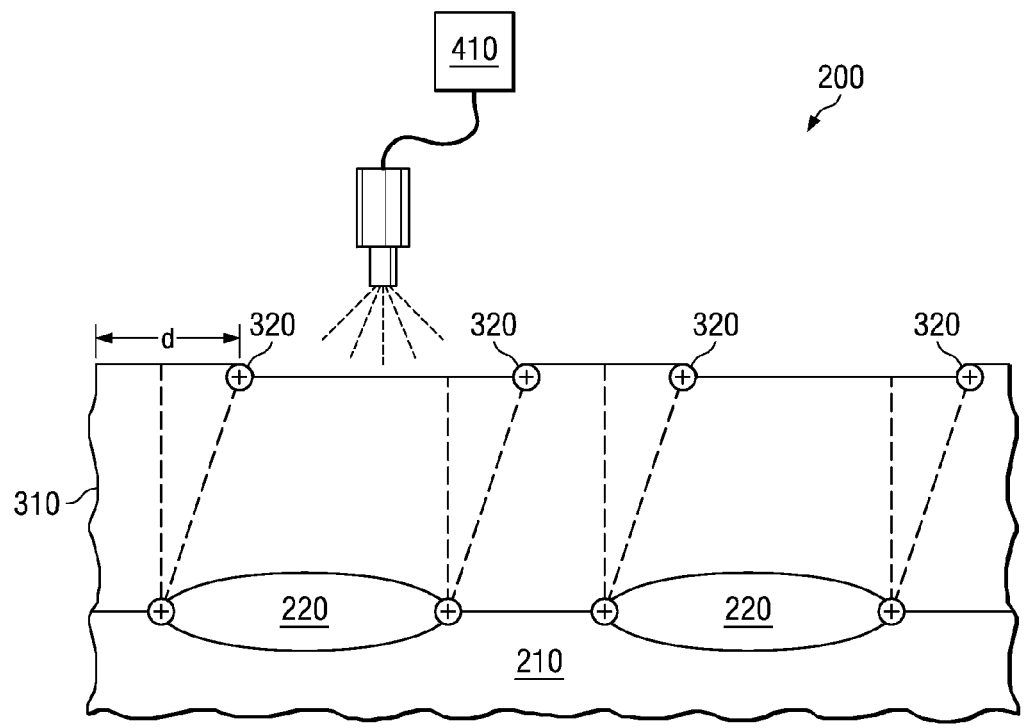

Turning now to FIG. 4, illustrated is the semiconductor device 200 of FIG. 3 as a location of the doped buried layers 220 relative to the surface features 320 is determined using a scatterometer 410. In the embodiment shown, a lateral location of the doped buried layers 220, which are sub-surface features, is determined with respect to a lateral location of the surface features 320. For example, the location of the doped buried layers 220 may be determined immediately after formation of the epitaxial layer 310, for example prior to forming any additional features in, on or over the epitaxial layer 310.

Scatterometry is a non-destructive wafer level measurement system that uses an energy source (e.g., a light source) emitted on specially designed grid patterns on a wafer surface. Through diffraction of the energy source on known grid line/space features, a detector may collect reflected energy and discern the grid dimensions. While this method is routinely used to measure photo/etch dimensions for wafer surface defined features, heretofore the present invention such a techniques hasn't been used to measure dimensions, nonetheless locations of sub-surface features (e.g., measure the alignment of sub-surface features relative to surface features), such as the doped buried layers 220 of the present embodiment.

Accordingly, and in accordance with the principles of the present invention, the scatterometer may be used to assist with lattice shift alignment. For instance, the surface features 320 created during the processing of the doped buried layers 220 and thereafter during the formation of the epitaxial layer 310 may be used to generate a grid feature comprised of the surface features 320 and the doped buried layers 220. The scatterometer may then be used to discern the dimensions of the resulting grid, which provides a location of the doped buried layers 220 relative to the surface features 320. Thus, not only may the location of the doped buried layers 220 be ascertained, the epitaxial lattice shift (d) of the epitaxial layer 310 may also be determined.

For instance, given that the properties of solids change with composition of the material, the subsurface discernment of the edge of the doped buried layer 220 may be achieved. For example, given a Silicon substrate and an N-Type buried layer (e.g., Phosporous or Antimony), the optical constants of the substrate (n, k constants as an example) generally meaningfully change between the undoped region of Silicon and the N-buried layer region. This provides the sub-surface edge of the alignment measurement. During formation of the buried layer, typical process steps would include dopant implantation followed by an oxidation that is thereafter stripped of oxide to allow epitaxial growth. Given that the oxidation rate of the Silicon is highly dependent on doping concentration, a step in the surface of the substrate (post buried layer implant and pre epitaxial deposition) is formed. This step may be tens of nanometers for a typical process. This creates the top surface edge of the alignment measurement. When the respective edges of above described features are arranged in repeating lines and spaces (e.g., grid structures), Scatterometry can be used to determine physical dimensions (in this case alignment of surface to sub-surface layers).

Accordingly, the method enables a non-destructive direct measurement of lattice alignment after forming the epitaxial layer 310. Additionally, the scatterometry process may be conducted on product wafers, as opposed to test wafers as is the case in the traditional determination processes. Moreover, after determining the parameters needed to detect the sub-surface features, in this instance the doped buried layers 220, the process is relatively simple to implement.

Figure 5:
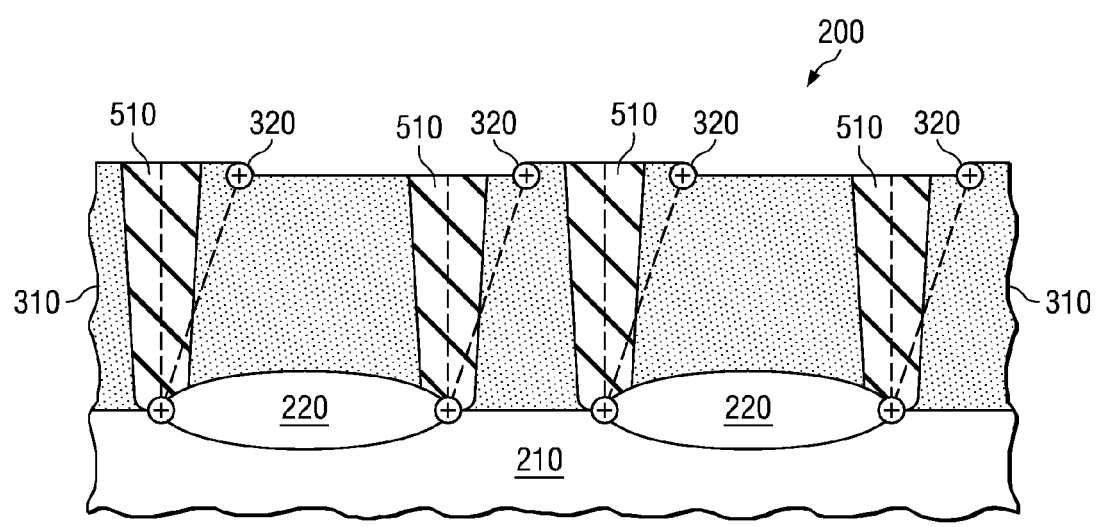

Turning now to FIG. 5, illustrated is the semiconductor device 200 of FIG. 4 after forming one or more additional features 510 over, on or in the epitaxial layer 310 using the determined location of the doped buried layers 220. In the given embodiment of FIG. 5, the one or more additional features 510 are isolation well features aligned with respect to the doped buried layers 220. Knowing the specific location of the doped buried layers 220, for example using the scatterometer as described above, the isolation well features may be aligned so as to reduce, if not eliminate, any misalignment between the doped buried layers 220 and the isolation well features. Accordingly, at least in this embodiment, the leakage paths, as well as changes in high voltage component capability, may be substantially reduced.

Those skilled in the art understand, at least after knowing the location of the doped buried layers 220 using the inventive aspects of the present invention, the different processes and techniques that might be used to form the one or more additional features—in this embodiment isolation well features. For instance, in one embodiment a mask layer and high dose implant is used to form the isolation well features at precise locations relative to the doped buried layers 220. In this example, the determined location of the doped buried layers 220 might be used to appropriately and accurately pattern the mask layer, and thereafter a conventional high dose implant might be used to form the isolation well features within the epitaxial layer 310.

Figure 6:
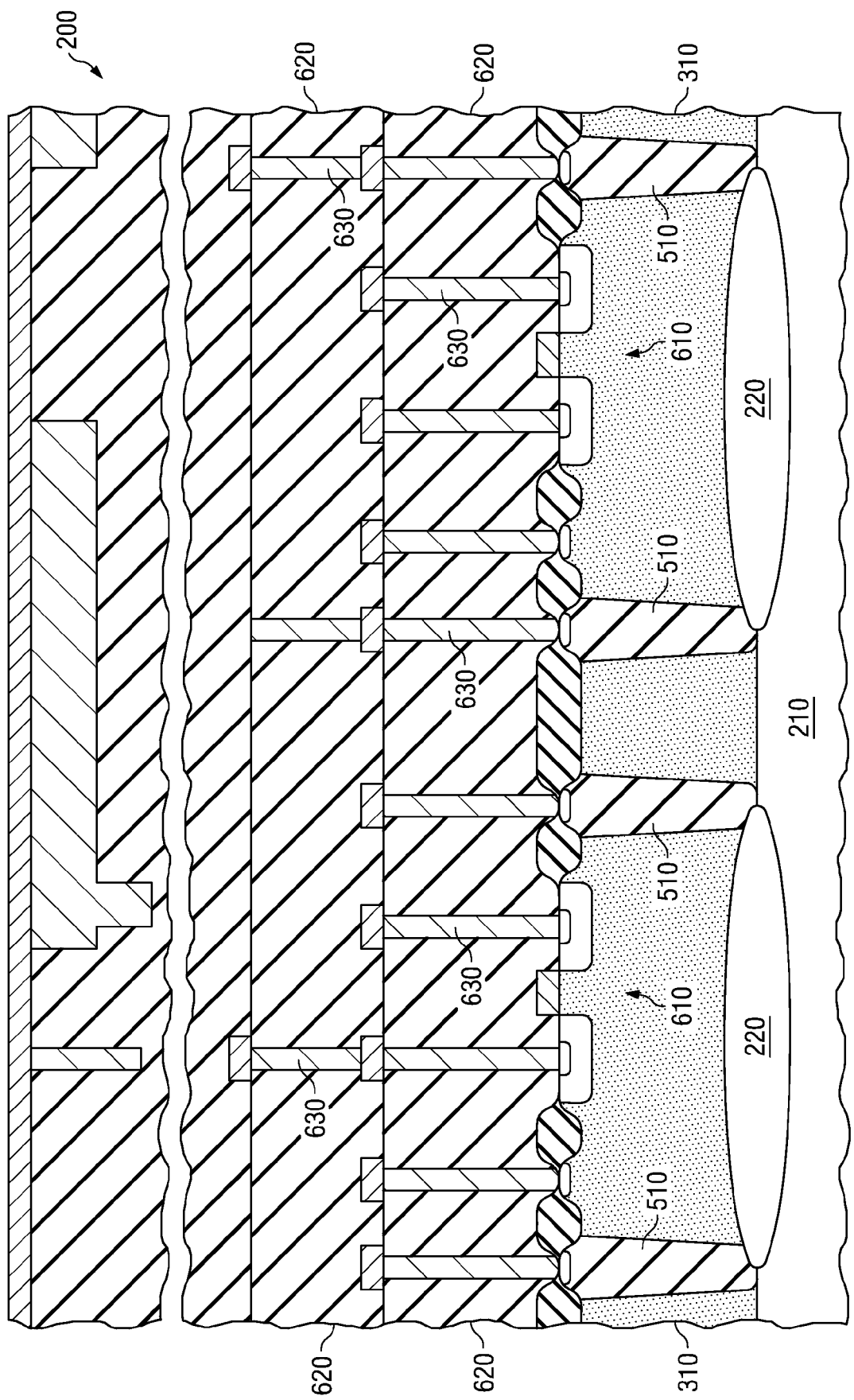

Turning lastly to FIG. 6, illustrated is the semiconductor device 200 of FIG. 5 after forming transistor features 610 in, on and/or over the epitaxial layer 310. Additionally formed over the transistor features 610 are dielectric layers 620, as well as interconnects 630 located within the dielectric layers 620 for contacting the transistor features 610. The resulting structure of FIG. 6, without being limited to the illustrated transistor features 610, dielectric layers 620, or interconnects 630, as well as their method of manufacture, is the semiconductor device 200 configured as an integrated circuit.

Those skilled in the art to which the invention relates will appreciate that other and further additions, deletions, substitutions and modifications may be made to the described embodiments without departing from the scope of the invention.

What is claimed is:

1. A method for manufacturing a semiconductor device, comprising:
   providing a substrate;
   forming an epitaxial layer having a sub-surface feature and a surface feature, such that the epitaxial layer directly contacts the substrate and the sub-surface feature; and
   using a scatterometer to direct an energy onto the epitaxial layer and to determine a lateral location of the sub-surface feature to determine a location of the sub-surface feature relative to a location of the surface feature using the scatterometer and only an energy reflected from the epitaxial layer.

2. The method as recited in claim 1 wherein using the scatterometer includes measuring a diffraction pattern of the sub-surface feature.

3. The method as recited in claim 1 wherein the sub-surface feature is a doped buried layer located between a wafer substrate and an epitaxial layer and the surface feature is a surface feature in the epitaxial layer.

4. The method as recited in claim 3 wherein the surface feature in the epitaxial layer is a relief feature associated with the doped buried layer and carried to the surface of the epitaxial layer during the formation of the epitaxial layer.

5. The method as recited in claim 4 wherein using the scatterometer to determine the location of the doped buried layer relative to the location of the surface feature further includes ascertaining a lateral shift in the epitaxial layer.

6. The method as recited in claim 3 wherein using the scatterometer occurs after formation of the epitaxial layer and before formation of any other feature over, on or in the epitaxial layer.

7. The method as recited in claim 3 further including forming an additional feature over, on or in the epitaxial layer using the determined location.

8. The method as recited in claim 7 wherein forming the additional feature includes aligning the additional feature with respect to the doped buried layer.

9. The method as recited in claim 8 wherein the additional feature is an isolation well feature.

10. A method for manufacturing a semiconductor device, comprising:
    providing a wafer substrate having a doped buried layer located there over;
    forming an epitaxial layer in direct contact with the doped buried layer and the wafer substrate, the epitaxial layer having a surface feature;
    using a scatterometer to direct an energy onto the epitaxial layer to determine a lateral location of the doped buried layer to determine a location of the doped buried layer relative to a location of the surface feature using the scatterometer and only an energy reflected from the epitaxial layer; and
    forming an additional feature over, on or in the epitaxial layer at a location based on the determined location of the doped buried layer.

11. The method as recited in claim 10 wherein using the scatterometer includes measuring a diffraction pattern of the doped buried layer.

12. The method as recited in claim 10 wherein the surface feature in the epitaxial layer is a relief feature associated with the doped buried layer and carried to the surface of the epitaxial layer during the formation of the epitaxial layer.

13. The method as recited in claim 12 wherein using the scatterometer to determine the location of the doped buried layer relative to the location of the surface feature further includes ascertaining a lateral shift in the epitaxial layer.

14. The method as recited in claim 10 wherein using the scatterometer occurs after formation of the epitaxial layer and before formation of any other feature over, on or in the epitaxial layer.

15. The method as recited in claim 10 wherein forming the additional feature includes aligning the additional feature with respect to the doped buried layer.

16. The method as recited in claim 15 wherein the additional feature is an isolation well feature.

17. A method for manufacturing a semiconductor device, comprising:
- providing a substrate having an area defined by a perimeter;
- providing a sub-surface feature within the perimeter;
- providing a continuous epitaxial layer having a surface feature, wherein the continuous epitaxial layer covers the entire substrate within the perimeter;
- using a scatterometer to direct an energy within the perimeter; and
- determining a location of the sub-surface feature relative to the surface feature using the scatterometer and only an energy reflected from within the perimeter.

* * * * *